United States Patent
Kankan et al.

(10) Patent No.: US 9,150,499 B2
(45) Date of Patent: Oct. 6, 2015

(54) PROCESS FOR THE PREPARATION OF NATEGLINIDE

(75) Inventors: Rajendra Narayanrao Kankan, Maharashtra (IN); Dharmaraj Ramachandra Rao, Maharashtra (IN); Dilip Ramdas Birari, Maharashtra (IN)

(73) Assignee: Cipla Limited, Mumbai (IN)

( * ) Notice: Subject to any disclaimer, the term of this patent is extended or adjusted under 35 U.S.C. 154(b) by 52 days.

(21) Appl. No.: 13/703,758

(22) PCT Filed: Jun. 14, 2011

(86) PCT No.: PCT/GB2011/000895
§ 371 (c)(1),
(2), (4) Date: Feb. 28, 2013

(87) PCT Pub. No.: WO2011/157986
PCT Pub. Date: Dec. 22, 2011

(65) Prior Publication Data
US 2013/0165686 A1    Jun. 27, 2013

(30) Foreign Application Priority Data

Jun. 14, 2010  (IN) .................... 1793/MUM/2010

(51) Int. Cl.
*C07C 229/00* (2006.01)
*C07C 231/12* (2006.01)

(52) U.S. Cl.
CPC ........... *C07C 231/12* (2013.01); *C07C 2101/14* (2013.01)

(58) Field of Classification Search
CPC .................................................. C07C 229/00
See application file for complete search history.

(56) References Cited

U.S. PATENT DOCUMENTS

| | | | |
|---|---|---|---|
| 4,816,486 A | 3/1989 | Takai et al. | |
| RE34,878 E | 3/1995 | Toyoshima et al. | |
| 5,463,116 A | 10/1995 | Sumikawa et al. | |
| 7,208,622 B2 | 4/2007 | Takahashi et al. | |
| 7,425,648 B2 | 9/2008 | Vigano' et al. | |
| 7,605,180 B2 | 10/2009 | Ninomiya et al. | |
| 7,767,847 B2 | 8/2010 | Gazdag et al. | |
| 2003/0229249 A1 | 12/2003 | Sumikawa et al. | |
| 2010/0004235 A1* | 1/2010 | Schirok et al. | 514/234.2 |

FOREIGN PATENT DOCUMENTS

| EP | 0196222 | * 10/1986 |
|---|---|---|
| EP | 1334962 A1 | 8/2003 |
| WO | 2005005373 A1 | 1/2005 |
| WO | 2005121071 A1 | 12/2005 |
| WO | 2008096373 A2 | 8/2008 |
| WO | 2011157986 A1 | 12/2011 |

OTHER PUBLICATIONS

Ray et al. (Synthesis and Applications of Isotopically Labelled Compounds, Proceedings of the International Symposium, 7th, Dresden, Germany, Jun. 18-22, 2000 (2001), Meeting Date 2000, 228-231).*
Foreign communication from a related counterpart application—International Search Report and Written Opinion, PCT/GB2011/000895 dated Jul. 28, 2011, 9 pages.
Foreign communication from a related counterpart application—International Preliminary Report on Patentability, PCT/GB2011/000895 dated Dec. 14, 2012, 6 pages.
Certified priority document for Indian patent application entitled "A Process for Preparation of Chirally Pure (−)-N-(Trans-4-Isopropylcyclohexyl-1-Carbonyl)-D-Phenylalanine," by Rajendra Narayanrao Kankan, et al., filed Jun. 14, 2010 as Indian application No. 1793/MUM/2010.
Indian patent application entitled "An Improved Process for the Preparation of N-(Trans-4-Isopropylcyclohexylcarbonyl)-D-Phenyl Alanine and Intermediates Thereof," filed on May 12, 2007 as Indian application No. 2380/MUM/2007.
Indian patent application entitled "A Novel Process for the Preparation of N-(Trans-4-Isopropylcyclohexyl Carbonyl)-D-Phenyl-Alanine(Nateglinide)," filed on May 3, 2003 as Indian application No. 177/MAS/2003.

* cited by examiner

*Primary Examiner* — Sudhakar Katakam
*Assistant Examiner* — Jennifer C Sawyer
(74) *Attorney, Agent, or Firm* — Conley Rose, P.C.; Rodney B. Carroll (57) ABSTRACT

The present invention relates to a process for the preparation of substantially pure nateglinide of formula (I), substantially free from the cis-isomer and L-enantiomer and preparation of enantiomerically pure nateglinide form B, directly from the hydrolysis of a (−)-N-(trans-4-isopropylcyclohexyl-1-carbonyl)-D-phenylalanine alkyl ester in a ketonic solvent or water or mixture thereof.

19 Claims, 2 Drawing Sheets

PROCESS FOR THE PREPARATION OF NATEGLINIDE

CROSS-REFERENCE TO RELATED APPLICATIONS

This application is a filing under 35 U.S.C. 371 of International Application No. PCT/GB2011/000895 filed Jun. 14, 2011, entitled "A Process for the Preparation of Nateglinide," which claims priority to Indian Patent Application No. 1793/MUM/2010 filed on Jun. 14, 2010, which applications are incorporated by reference herein in their entirety.

TECHNICAL FIELD OF THE INVENTION

The present invention relates to a process for the preparation of chirally-pure (−)-N-(trans-4-isopropylcyclohexyl-1-carbonyl)-D-phenylalanine (nateglinide).

BACKGROUND

Nateglinide is a new class of antidiabetic drug developed jointly by Ajinomoto Co. Inc. and Hoechest Marion Russel of Japan. Its blood sugar lowering effect is rapid following oral administration, since it is short-acting, it prevents hypoglycemia between meals. Nateglinide is indicated to lower blood glucose in patients with type 2 diabetes, where hypoglycemia cannot be adequately controlled by diet, physical exercise and α-glucosaccharase inhibitors.

Nateglinide is chemically termed as (−)-N-(trans-4-isopropylcyclohexyl-1-carbonyl)-D-phenylalanine which is represented by the following formula (I).

Nateglinide was first disclosed in the U.S. Pat. No. 4,816,486 (RE34878).

US20060148902A1 describe hydrolysis of a nateglinide methyl ester in a mixture of water and toluene in the presence of phase transfer catalysts and KOH followed by addition of dilute HCl, filtration, and drying to afford Form B.

U.S. Pat. No. 7,208,622 describes a process in which trans-4-isopropylcyclohexane carbonyl chloride (i.e. a derivative of trans-4-isopropylcyclohexane carboxylic acid) is reacted with D-phenylalanine in the presence of a caustic solution followed by acidification in a mixture of water and acetone and crystallization at 58-72° C. which results in Form H of nateglinide.

Indian application 177/MAS/2003A discloses a process for preparing nateglinide comprising: condensation of D-phenyl alanine methyl ester with trans-4-isopropyl-cyclohexylcarboxylic acid chloride in the presence of a halo solvent such as chloroform and a base (TEA, triethylamine) followed by alkali metal hydrolysis in an alcoholic solvent such as isopropanol. The resulting nateglinide contains the cis isomer and the L-isomer in an amount <0.05%. However, on following the methodology as disclosed in examples 1 and 2, it was observed that, the L-isomer content does not go below 0.22%. This is due to the use of alkali metal hydroxide in the hydrolysis step at ambient temperature. Further, the use of isopropanol in example 2, yields isopropyl ester of nateglinide on acidification with hydrochloric acid. Further, excess D-phenyl alanine methyl ester may either lead to formation of dimeric impurity of formula (D)

during coupling reaction or remains as impurity in the nateglinide ester which needs to be removed by HCl washing prior to hydrolysis.

Indian application 2007/MUM/02380 discloses a process which involves treating an alkyl ester of D-phenylalanine or its acid addition salt with trans-4-isopropylcyclohexanecarboxylic acid halide under biphasic conditions in the presence of a base to give nateglinide alkyl ester, which is hydrolyzed to nateglinide having chiral purity 99.9-100.0%.

US20070043117A1 discloses a process for the preparation of chirally pure nateglinide G, whereby after alkaline hydrolysis of nateglinide alkyl ester, in the mixture of methanol-water; mineral acid is added in two portions such that, in first place mixture of nateglinide base and its alkali salt is isolated whereas in the next step chirally pure nateglinide base is isolated. Thus the process requires two steps to isolate chirally pure nateglinide. Further, the mixture of nateglinide base and it's alkali salt is sticky in nature and hence filtration takes prolong time.

Nateglinide preparation is also disclosed in U.S. Pat. No. 5,463,116, US2004014815A, US2003229249A and WO2008096373.

Most of the prior art methods use a combination of an alkali metal hydroxide and alcoholic solvents during hydrolysis of nateglinide and crystallization of nateglinide. The major drawback of using alcoholic solvents is that some of the nateglinide esterifies back to nateglinide alkyl ester. Further, nateglinide obtained by following the prior art process, is contaminated with cis-isomer, L-isomer, and/or N-(4-isopropyl benzoyl)-D-phenyl alanine (an ethyl analog of nateglinide and dimer impurity), hence repetitive purifications are required to obtain the purified product. This further, thus, reduces yield and purity of the product.

Therefore there is a need to develop a process for the synthesis of nateglinide that overcomes the problems of prior art and that which is simple, cost effective, non-hazardous and industrially viable.

OBJECTIVES OF THE INVENTION

Therefore it is an object of the present invention to provide a process for preparation of (−)-N-(trans-4-isopropylcyclo- hexyl-1-carbonyl)-D-phenylalanine (nateglinide) which is substantially free from related impurities, cis-isomer and L-enantiomer.

Another object of the present invention is to provide an industrially-advantageous process for the preparation of pure nateglinide Form B.

Yet another object of the present invention is to provide safe, high yielding, high purity and industrially viable method than any method yet known.

SUMMARY OF THE INVENTION

According to a first aspect of the present invention, there is provided a process for preparing nateglinide of formula (I) or a pharmaceutically acceptable salt thereof, which process comprises hydrolysis of (−)-N-(trans-4-isopropylcyclohexyl-1-carbonyl)-D-phenylalanine alkyl ester of formula (II)

in the presence of a solvent comprising a ketone, water or a mixture thereof, wherein the Alk group is a C1-C4 alkyl group. Optionally, the process further comprises converting the nateglinide (I) to a pharmaceutically acceptable salt thereof, Advantageously, the nateglinide is substantially free from related impurities, for example the cis-isomers and L-enantiomers.

The Alk group is a C1-C4 alkyl group. Suitably, Alk is methyl, ethyl, straight- or branched-chain propyl, or straight- or branched-chain butyl. Preferably Alk is methyl or ethyl, most preferably methyl. In this specification, where Alk is depicted as methyl, it is to be understood that the same process would apply to any C1-C4 alkyl group.

In an embodiment, the hydrolysis is carried out at a temperature ranging from 0° C. to 30° C. Preferably, the hydrolysis is carried out at a temperature ranging from 0° C. to 20° C., more preferably at a temperature ranging from 5° C. to 10° C.

Preferably, the solvent is a mixture of a ketone and water, and the ketone:water ratio varies from 5:1 to 1:1 v/v, preferably 1:1 v/v. Most preferably, the solvent is a mixture of acetone and water.

In an embodiment, the solvent is a 1:1 v/v mixture of acetone and water, isolation of the nateglinide comprises drying under vacuum tray driers at a temperature ranging from 70° C. to 90° C., and the nateglinide is isolated in polymorphic Form B.

In an embodiment, the reaction mass after hydrolysis is treated with an acid (preferably HCl) to obtain nateglinide of formula (I). Suitably, the acid is added until the pH of the reaction mass is adjusted to 2-3. This is typically carried out at a temperature ranging from about 0° C. to about 20° C., more preferably at a temperature ranging from about 10 to about 15° C., most preferably at a temperature of about 10° C.

In an embodiment, the compound of formula (II) is prepared by converting the D-phenyl alanine methyl ester of formula (IV)

to the compound of formula (II). The conversion may involve condensation of D-phenyl alanine methyl ester of formula (IV), either in the salt form (typically the hydrochloride) of formula (IVa) or as the free base of formula (IVb)

with trans-4-isopropyl-cyclohexylcarboxylic acid of formula (III)

using a condensing agent in the presence of a solvent to form an amide of formula (II), which may be further purified using a C1-C4 alcohol. Alk has the same meanings as given above and X is an acid which forms an acid addition salt with compound (IV).

In an embodiment, the compound (IV) is in the form of an HCl addition salt (i.e. X is HCl).

In an embodiment, the trans-4-isopropyl-cyclohexylcarboxylic acid of formula (III) is in molar excess relative to the compound (IV).

In an embodiment, the condensing reagent is selected from the group consisting of phenylsilane, 1,1'-carbonyldiimidazole (CDI), benzotriazol-1-yloxytris (dimethylamino) phosphonium hexafluorophosphate (BOP), 1-hydroxy benzotriazole hydrate (HOBt), PyBOP (Analog of the BOP), 1,3-dicyclohexylcarbodiimide (DCC), 1,3- diisopropylcarbodiimide (DIC), N,N-diisopropylethylamine (DIEA), 4-dimethylaminopyridine (DMAP), 1,4-dithio-L-threitol (DTT), N-ethyl-N'-(3-dimethylaminopropyl)carbodidiimide hydrochloride (EDC HCl), 2-(7-aza-1H-benzotriazole-1-yl)-1,1,3,3-tetramethyluroniumhexafluorophosphate (HATU), 2-(1H-benzotriazole-1-yl)-1,1,3,3-tetramethyluronium hexafluorophosphate (HBTU), 2-(6-chloro-1H-benzotriazole-1-yl)-1,1,3,3-tetramethylaminiumhexafluorophosphate (HCTU), O-(benzotriazol-1-yl)-N,N,N',N'-tetramethyluronium tetrafluoroborate (TBTU), tetramethylfluoroformamidiniunhexafluorophosphate (TFFH) and mixtures thereof. Preferably, the condensing reagent is a mixture of DCC and HOBT. Suitably, a sub-molar quantity of HOBT per mole of compound (IV) is used in the condensation. Preferably, between around 0.1 and 0.9 moles of HOBT per mole of compound (IV) are used, more preferably between around 0.2 and 0.5 moles are used, most preferably around 0.3 moles of HOBT per mole of compound (IV) are used.

Suitably, the condensation solvent is a halogenated solvent, a polar solvent or a mixture thereof. Preferably, the condensation solvent is selected from the group consisting of chloroform, dichloromethane, dimethylformamide, dimethylacetamide, dimethyl sulfoxide, N-methyl pyrrolidone, sulfolane, diglyme, 1,4-dioxane, tetrahydrofuran, acetonitrile, acetone and mixtures thereof. Most preferably, the condensation solvent is MDC.

Suitably, the condensation step is carried out at a temperature ranging from about −5 to about 30° C. Preferably, the condensation step is carried out at a temperature ranging from about 0° C. to about 20° C., more preferably at a temperature ranging from about 10 to about 15° C.

After completion of the condensation reaction, the excess acid of formula (III) and HOBT may be removed by washing the reaction mass with alkali, preferably with an aqueous solution of an alkali metal hydroxide, an alkali metal carbonate or aqueous ammonia. Suitably, the alkali is an aqueous solution of sodium hydroxide.

In an embodiment, the alkali metal hydroxide is selected from the group consisting of sodium hydroxide, potassium hydroxide, caecium hydroxide, magnesium hydroxide, lithium hydroxide, barium hydroxide and calcium hydroxide, preferably sodium hydroxide.

Advantageously, the compound (II) is purified in a C1-C4 alcohol prior to the hydrolysis step. Suitably, the alcohol is methanol or ethanol. Preferably, the alcohol is methanol. The purification step may be carried out at a temperature ranging from about 30° C. to about 50° C.

In an embodiment, the compound (IV) is isolated as an acid addition of formula (IVa) and used as the salt form in the condensation to form compound (II). Alternatively, the compound (IV) is prepared as an acid addition salt of formula (IVa), converted to the free base of formula (IVb) and compound (IVb) used in the condensation to form compound (II)

(IVa)

(IVb)

wherein X in compound (IVa) is an acid and Alk has the same meaning as defined above. Preferably, the acid X is HCl. When the compound (IVa) is converted to the free base (IVb), the conversion to the free base may comprise neutralizing of the acid addition salt with aqueous ammonia.

In an embodiment, the compound of formula (II) is isolated from the reaction mixture by distilling off excess solvent and isolating in a non-polar solvent. Suitably, the non-polar solvent is selected from the group consisting of toluene, n-hexane, n-heptane, 1,4-dioxane, chloroform and diethyl ether. Preferably, the non-polar solvent is n-hexane.

In an embodiment, the compound of formula (IV) is prepared by esterification of D-phenyl alanine of compound of formula (V)

(V)

The esterification may be carried out in methanol with thionyl chloride. Suitably, the esterification is carried out at a temperature ranging from about 0° to about 30° C., preferably from about 5 to 10° C. Typically, the esterification reaction takes about 12 to about 15 hours.

The process of the present invention for preparing nateglinide reduces or substantially eliminates isomeric impurities, especially the corresponding cis-isomer and the corresponding L-enantiomer. In an embodiment, the term "substantially pure" in the specification refers to a substance that has preferably between about 95% and 100% of one form (either cis or trans; preferably the trans). and between about 5% and 0% of the other form, more preferably between about 99% and 100% of one form (either cis or trans) and between about 1% and 0% of the other form, and, most preferably, between about 99.8% and 100% of one form (either cis or trans) and about 0.2% and 0% of the other form.

In a preferred embodiment, the nateglinide of formula (I) obtained by the process of the present invention has less than 0.5% of N-(cis-4-isopropylcyclohexyl-1-carbonyl)-D-phenylalanine, preferably less than 0.3% and more preferably less than 0.2%.

In a preferred embodiment, the nateglinide of formula (I) obtained by the process of the present invention has less than 0.5% of N-(trans-4-isopropylcyclohexyl-1-carbonyl)-L-phenylalanine, preferably less than 0.3% and more preferably less than 0.2%.

Advantageously, the condensation step does not induce racemization.

Advantageously, the compound of formula (II) is free of dimeric impurity of formula (D)

(D)

In an embodiment, the nateglinide of formula (I) obtained by the process of the present invention is in the polymorphic Form B. Preferably, the nateglinide Form B is substantially free from other polymorphs. Advantageously, no further purification nor crystallization is required to prepare pure nateglinide polymorphic Form B and this forms another aspect of the present invention. The physical characteristics of Form B of nateglinide are as defined in US20060148902A1.

Yet another aspect of the present invention relates to a safe, high-yielding, high-purity and industrially-viable method than any method yet known.

The nateglinide formed by the processes described above may be combined with a suitable carrier to make a pharmaceutical composition. Such compositions may be used to lower blood glucose in patients with type 2 diabetes. According to another aspect of the present invention, there is provided a pharmaceutical composition comprising nateglinide prepared by one of the processes described above together with one or more pharmaceutically-acceptable excipients.

According to another aspect of the present invention, there is provided nateglinide prepared by one of the processes described above for use in medicine. Suitably, the nateglinide is for use in lowering blood glucose in patients with type 2 diabetes.

According to another aspect of the present invention, there is provided the use of nateglinide prepared by one of the processes described above in the manufacture of a medicament for lowering blood glucose in patients with type 2 diabetes.

According to another aspect of the present invention, there is provided a method of lowering blood glucose in patients with type 2 diabetes comprising administering to a patient in need thereof an effective amount of nateglinide prepared by one of the processes described above.

DETAILED DESCRIPTION OF THE INVENTION

The process according to the present invention will now be described in more detail below.

In a preferred embodiment, the process for the preparation of nateglinide according to the present invention is depicted in the reaction scheme below.

R.T. = room temperature, i.e. around 25° C.
MDC = dichloromethane
DCC = dicyclohexylcarbodiimide
HOBt = 1-hydroxybenzotriazole hydrate

[Bracket indicates intermediate that could be isolated in the integrated process].

Accordingly, in an embodiment, the present invention provides a process for the synthesis of substantially pure nateglinide of formula (I), the process comprising a first step (i) of esterification of D-phenyl alanine of compound of formula (V) with thionyl chloride in methanol to obtain D-phenyl alanine methyl ester compound of formula (IV) in a salt form (typically the hydrochloride) of formula (IVa) or the free base of formula (IVb).

The esterification may involve reacting D-phenyl alanine with thionyl chloride in methanol at a temperature of 0-30° C., preferably at 5-10° C. for 12-15 hours. Use of thionyl chloride at a lower temperature of 0-30° C. results in a high yield of the ester of formula (IV), in comparison with other ester-forming methods of amino acids. It further helps in complete conversion of D-phenyl alanine and overall increase in the yield and purity as compared to sulphuric acid, hydrochloric acid etc. Further, it reduces the number of reaction hours from 48-50 hours to 12 hours.

After completion of the reaction, the compound of formula (IV) may be isolated as a hydrochloride salt (IVa) by evaporation of solvent which can either be used directly in the next condensing step or can be further converted to its free base of formula (IVb) by neutralizing the salt with a suitable reagent, for example aqueous ammonia, prior to the reaction with trans-4-isopropyl-cyclohexylcarboxylic acid. Preferably, in the process of the present invention, the compound of formula (IV) is isolated as free base (IVb) without isolation of salt of formula (IVa) which may be taken up for condensing reaction.

In an embodiment, step (ii) comprises condensation of the D-phenyl alanine methyl ester compound of formula (IV) with trans-4-isopropyl-cyclohexylcarboxylic acid of formula (III) using a suitable condensing agent in the presence of a suitable solvent to form an amide (−)-N-(trans-4-isopropyl-cyclohexyl-1-carbonyl)-D-phenylalanine methyl ester of formula (II).

In the prior art processes, the amine of formula (IV) is coupled with a derivative of trans-4-isopropyl-cyclohexylcarboxylic acid of formula (III) such as trans-4-isopropyl-cyclohexylcarboxylic acid chloride or the N-hydroxysuccinmide ester of trans-4-isopropyl-cyclohexylcarboxylic acid. This involves the use of an expensive reagent such as N-hydroxysuccinimide.

In an embodiment, D-phenyl alanine methyl ester compound of formula (IV) is directly coupled with trans-4-isopropyl-cyclohexylcarboxylic acid of formula (III) without intermediate conversion to an acid chloride or an N-hydroxysuccinimide ester, of formula (III). The coupling is suitably carried out in the presence of a condensing reagent and an inert organic solvent, to obtain nateglinide ester of formula (II). Thus the process step avoids the use of an expensive reagent such as N-hydroxysuccinimide. Also, it reduces the number of synthetic steps, which is a preferred embodiment of the present invention.

Further, the prior art processes use excess moles of amine which may either lead to formation of dimeric impurity of formula (D), during the coupling reaction or remain as contaminant in nateglinide ester which needs to be removed before the hydrolysis step.

However, in a preferred embodiment of the process of present invention, the molar ratio of 4-isopropyl-cyclohexylcarboxylic acid (III) is in excess of that of the amine of formula (IV), which avoids formation of dimer (D). Further, excess acid can be easily removed by alkali wash or by purification in suitable solvent. And this forms another preferred embodiment of the present invention.

A suitable condensing reagent in step (ii) according to the present invention may be selected from the group consisting of phenylsilane, 1,1'-carbonyldiimidazole (CDI), benzotriazol-1-yloxytris (dimethylamino) phophonium hexafluorophosphate (BOP), 1-hydroxy benzotriazole hydrate (HOBt), PyBOP (Analog of the BOP), 1,3-dicyclohexylcarbodiimide (DCC), 1,3-diisopropylcarbodiimide (DIC), N,N-diisopropylethylamine (DIEA), 4-dimethylaminopyridine (DMAP), 1,4-dithio-L-threitol (DTT), N-ethyl-N'-(3-dimethylaminopropyl)carbodidimide hydrochloride (EDC HCl), 2-(7-aza-1H-benzotriazole-1-yl)-1,1,3,3-tetramethyluronium-hexafluorophosphate (HATU), 2-(1H-benzotriazole-1-yl)-1, 1,3,3-tetramethyluronium hexafluorophosphate (HBTU), 2-(6-chloro-1H-benzotriazole-1-yl)-1,1,3,3-tetramethylaminiumhexafluorophosphate (HCTU), O-(benzotriazol-1-yl)-N,N,N',N'-tetra methyluronium tetrafluoroborate (TBTU), tetramethylfluoroformamidiniunhexafluorophosphate (TFFH) and mixtures thereof. In a preferred embodiment, DCC is used in combination with HOBT to increase the overall coupling power.

It was observed that use of HOBT in the coupling reaction prevents racemization; whereas in the absence of HOBt, the L-isomer content increases to 1.5%. Preferably, 0.1 to 0.5 molar equivalents and more preferably 0.3 molar equivalents of HOBt per mole of compound of formula (IV), is used in the coupling reaction.

A suitable inert organic solvent for step (ii) according to the present invention, is selected from the group consisting of a halogenated (solvent such as chloroform, or dichloromethane (MDC)); a polar solvent (such as dimethylformamide (DMF), dimethylacetamide, dimethyl sulfoxide (DMSO), N-methyl pyrrolidone, sulfolane, diglyme, 1,4-dioxane, tetrahydrofuran, acetonitrile, acetone); and mixtures thereof. In a preferred embodiment, a halogenated solvent is used.

The process is carried out at a suitable temperature preferably until amine of formula (IV) is undetectable. Preferably, the reaction is carried out at a temperature in the range of −5 to 30° C., more preferably at a temperature in the range of 10 to 15° C.

After completion of the reaction, the excess acid of formula (III) and HOBT are removed by washing with alkali.

Suitably, the alkali is an aqueous solution of an alkali metal hydroxide such as sodium hydroxide, potassium hydroxide, cesium hydroxide, magnesium hydroxide, lithium hydroxide, barium hydroxide or calcium hydroxide. The alkali may also be an alkali metal carbonate such as sodium carbonate, sodium bicarbonate, calcium carbonate, potassium carbonate or aqueous ammonia. Preferably, the alkali is an aqueous solution of sodium hydroxide.

Nateglinide methyl ester of formula (II) is easily isolated from the reaction mixture, for example by distilling off excess solvent and isolating in a non-polar solvent.

Suitably, the non-polar solvent is selected from toluene, n-hexane, n-heptane, 1,4-dioxane, chloroform or diethyl ether. Preferably, the non-polar solvent is n-hexane.

It was observed that when coupling reaction is carried out without isolation of salt of D-phenyl alanine methyl ester compound of formula (IVa), it may retain same amount of L-isomer in the nateglinide methyl ester of formula (II). This L-isomer content is more when compared with coupling reaction carried out by isolation of salt of D-phenyl alanine methyl ester compound of formula (IVa). This indicates that purity of D-phenyl alanine methyl ester compound of formula (IV) has no effect on additional increase in the L-isomer content in the coupling step. In other words coupling step does not induce racemization.

Alternatively, in the process of the present invention, the coupling reaction can be carried out without isolating the salt of D-phenyl alanine methyl ester compound of formula (IV).

In an embodiment, the process further comprises step (iii): purification of (−)-N-(trans-4-isopropylcyclohexyl-1-carbonyl)-D-phenylalanine methyl ester of formula (II) in a C1-C4 alcohol, preferably methanol.

In step (iii) of the present invention, nateglinide methyl ester of formula (II) so formed is further purified in a suitable solvent so as to reduce the impurities and L-isomer to a desired level before proceeding to the hydrolysis step. Accordingly, nateglinide ester of formula (II) is purified in a C1-C4 alcoholic solvent. Preferably the purification is best conducted in methanol. Advantageously, the use of methanol for purification reduces all related impurities to below 0.1%.

In an embodiment, the process further comprises step (iv): hydrolysis of (−)-N-(trans-4-isopropylcyclohexyl-1-carbonyl)-D-phenyl alanine methyl ester of formula (II) in a suitable polar aprotic solvent or water or mixture thereof, to obtain nateglinide of formula (I) substantially free from related impurities, especially cis and L-enantiomers.

It was observed that the formation of L-isomer takes place either at esterification step (i) or at hydrolysis step (iv). The amount of L-isomer could be reduced either by isolation of compound of formula (IV) or by purifying nateglinide ester of formula (II). However, it was surprisingly found that, the formation of L-isomer in step (iv) is solvent and temperature specific and could be reduced to desired level using appropriate solvent mixture.

Thus in the step (iv) of the present invention, hydrolysis of (−)-N-(trans-4-isopropylcyclohexyl-1-carbonyl)-D-phenylalanine methyl ester of formula (II) is carried out using alkali metal hydroxide, in the presence of a polar aprotic solvent or water or mixture thereof.

Suitably, the alkali metal hydroxide is selected from sodium hydroxide, potassium hydroxide, caecium hydroxide, magnesium hydroxide, lithium hydroxide, barium hydroxide or calcium hydroxide, preferably sodium hydroxide.

Preferably, the polar aprotic solvent is selected from ketone, THF, DMF, DMSO, acetonitrile or ethyl acetate, most preferably a ketone.

It was observed that ketonic solvents, more preferably acetone, either alone or in combination with water, control L-isomer formation. Thus in the preferred embodiment, acetone is used in combination with water to increase overall solvent power. The acetone and water ratio varies from 5:1 to 1:1, but preferably ratio of 1:1 is used.

Preferably, the hydrolysis reaction is carried out at a temperature in the range of 0-40° C., more preferably at a temperature in the range of 10-15° C. The reaction mass is then acidified to pH 2-3 with HCl at around 10° C. to obtain nateglinide of formula (I). Nateglinide isolated by filtration and subsequent drying at 80° C., is substantially free of cis isomer and L-enantiomer.

In an embodiment, the term "substantially free of" in the specification refers to nateglinide having purity (measured by HPLC) above 99.5%, preferably above about 99.7%, and more preferably above about 99.8%.

The precipitated solid is further dried at 80° C. under vacuum until the moisture content is below 0.5% to provide nateglinide in high yield and purity.

Both the solvent composition and the temperature of reaction mass during hydrolysis plays an important role in obtaining the desired polymorphic form and also useful in non-racemization of the resulting nateglinide.

In the preferred embodiment, the nateglinide of formula (I) obtained by the process of the present invention has less than 0.5% of N-(cis-4-isopropylcyclohexyl-1-carbonyl)-D-phenylalanine, preferably less than 0.3% and more preferably less than 0.2%.

In yet another preferred embodiment, the nateglinide of formula (I) obtained by the process of the present invention has less than 0.5% of N-(trans-4-isopropylcyclohexyl-1-carbonyl)-L-phenylalanine, preferably less than 0.3% and more preferably less than 0.2%.

Nateglinide of formula (I) obtained by the process of present invention is in the pure form B substantially free from other polymorphs. No further purification or crystallization is required to prepare pure nateglinide polymorphic form B. This forms another embodiment of the present invention.

Nateglinide thus isolated is of pharmaceutical grade having L-isomer content below 0.1% and having physiochemical characteristics corresponding to form B of nateglinide.

Throughout the specification (including in the examples):
Efficiency is equal to practical yield/theoretical yield expressed as a percentage
Chiral purity is measured by HPLC.
The % of L-isomer is measured by HPLC and is expressed as area %.

EXAMPLES

The present invention will be illustrated in more detail by the following examples, with the understanding that the scope of the invention is deemed non-limiting in any way.

Example 1

Preparation of D-Phenyl Alanine Methyl Ester Hydrochloride (Compound IVa)

To a chilled solution of methanol (1000 ml), was charged thionyl chloride (100 ml, 1.361 moles) at 5° C.±3° C. under nitrogen atmosphere. D-Phenyl alanine (100 grams, 0.602 moles) was added at 5° C.±3° C. and further stirred for 30 minutes. The temperature was raised to 25° C. The reaction mass was further stirred for 12 hours and concentrated at 50° C. under reduced pressure to form a residue. The residue was stirred in toluene (500 ml). The solid was isolated by filtration, washed with toluene (2×500 ml) and dried at 50-55° C. under vacuum to yield the desired product.
Yield=130.0 grams
Efficiency=100%
Chiral Purity=100%

Example 2

Preparation of D-Phenyl Alanine Methyl Ester Base

D-phenyl alanine methyl ester hydrochloride (130 grams, 0.6 moles) was stirred in dichloromethane (350 ml) at 25° C.±3° C. The reaction mass was then cooled to 10° C. and basified with aqueous ammonia (200 ml) at 10° C.±3° C. within 30 minutes. The reaction mass was further stirred and the organic phase was separated. The aqueous layer was extracted with MDC (300 ml). Combined organic phases were washed with water (300 ml), followed by saturated sodium chloride solution (300 ml). The organic phase was dried on sodium sulphate and concentrated at 35° C. under reduced pressure to obtain the product.
Yield=108.0 grams
Efficiency=100%

Example 3

Preparation of Nateglinide Methyl Ester without Using HOBT

Dissolved D-phenyl alanine methyl ester (108 grams, 0.6 moles) in dichloromethane (590 ml) at 25° C. under nitrogen atmosphere. The reaction mass was cooled to 0° C.±3° C. Trans-4-isopropyl cyclohexane carboxylic acid (103 grams, 0.605 moles) was added in one portion and stirred for 15 minutes to obtain a clear solution. A solution of N,N-dicyclohexyl carbodiimide (150 grams, 0.727 moles) in dichloromethane (310 ml) was added drop wise to reaction mass maintaining temperature below 5° C. The temperature of reaction mass was raised to 15° C. and stirred for 3 hours. The reaction mass was filtered through hyflo, washed with dichloromethane (310 ml). The clear filtrate was washed with 10% NaOH solution (2×300 ml), followed by water until neutral pH. The MDC layer was dried over sodium sulphate and concentrated at atmospheric pressure. To the residue was added n-hexane under stifling (1500 ml). The reaction mass was stirred for 1 hour at 25° C.±3° C. and solid was isolated by filtration, washed with hexane (310 ml), suck dried and further dried at 50° C. to yield the product.

Efficiency=88.54%
Chiral purity=98.5%
L-isomer=1.5%

Example 4

Preparation of Nateglinide Methyl Ester Using HOBT

D-phenyl alanine methyl ester (108 grams, 0.6 moles) was dissolved in dichloromethane (590 ml) at 25° C. under nitrogen atmosphere. 1-hydroxy benzotriazole (40 grams, 0.296 moles) was added in one portion at 25° C. and stirred for 15 minutes to obtain a clear solution. The reaction mass was cooled to 0° C.±3° C. Trans-4-isopropyl cyclohexane carboxylic acid (103 grams, 0.605 moles) was added in one portion and stirred for 15 min to obtain a clear solution. A solution of N,N-dicyclohexyl carbodiimide (150 grams, 0.727 moles) in dichloromethane (310 ml) was added drop wise to reaction mass maintaining temperature below 5° C. The temperature of reaction mass was raised to 15° C. and stirred for 3 hours. The reaction mass was filtered through hyflo, washed with dichloromethane (310 ml). The clear filtrate was washed with 10% NaOH solution (2×300 ml), followed by water until neutral pH. The MDC layer was dried over sodium sulphate and concentrated at atmospheric pressure. To the residue was added n-Hexane under stirring (1500 ml). The reaction mass was stirred for 1 hour at 25° C.±3° C. and solid was isolated by filtration, washed with hexane (310 ml), suck dried and dried at 50° C.

Yield=185.0 grams
Efficiency=93.6%
L-isomer=0.06%
Chiral purity=99.94%

Example 5

Purification of Nateglinide Methyl Ester

Nateglinide ester (185 grams) was stirred with methanol (590 ml) for 2 hours at room temperature. The reaction mass was cooled to 10° C. and stirred for 30 min. The solid was isolated by filtration, washed with chilled methanol (310 ml), suck dried for 1 hour and dried at 50° C.

Yield=152.0 grams.
% Yield=82.16%
Chiral purity=100%

Example 6

Preparation of Nateglinide Methyl Ester without Isolation of D-Phenyl Alanine Methyl Ester Hydrochloride To a chilled solution of methanol (500 ml), was charged thionyl Chloride (50 ml, 0.681 moles) at 5° C.±3° C. under nitrogen atmosphere. D-Phenyl alanine (50 grams, 0.301 moles) was added at 5° C.±3° C. and further stirred for 30 minutes. The temperature was raised to 25° C. The reaction mass was further stirred for 12 hours and concentrated at 50° C. under reduced pressure to obtain residue. Basified with aqueous ammonia, extracted with dichloromethane (250 ml×2), dried over sodium sulphate and concentrated to obtain D-phenyl alanine methyl ester hydrochloride.

Chromatographic Purity=95.4%
L-isomer=0.33%

This material is converted to nateglinide methyl ester following the process as disclosed in example 4 and subsequent purification in methanol as per example 5.

Yield=66 grams
Chromatographic purity=99.64%
L-isomer=0.05%
Efficiency=72.0%

Example 7

Preparation of Nateglinide methyl ester using O-(benzotriazol-1-yl)-N,N,N',N'-tetra methyluronium tetrafluoroborate (TBTU)

Stirred D-phenyl alanine methyl ester hydrochloride (10.0 grams, 0.046 moles), trans-4-isopropylcyclohexanecarboxylic acid (8.3 grams, 0.049 moles) and TBTU (16.4 grams, 0.051 moles) in dichloromethane (100 ml) at 25° C. under nitrogen atmosphere. The reaction mass was cooled to 0° C.±3° C. N,N'-Diisopropyl ethyl amine (25.0 ml, 0.14 moles) was added drop wise maintaining temperature below 5° C. Raised the temperature of reaction mass to 15° C. and stirred for 3 hours. The reaction mixture was washed with (2×100 ml) water. The MDC layer was dried over sodium sulphate and concentrated at atmospheric pressure. To the residue was added methanol (50.0 ml) and stirred for 1.0 hour at 25° C.±3° C. The solid was isolated by filtration, washed with methanol (50 ml), and dried at 50° C. to yield nateglinide methyl ester.

Yield=13.25 grams
Efficiency=86.0%
Chiral purity=100.0%

Example 8

Preparation of Nateglinide in Methanol

To a solution of Methanol (50.0 ml) was added Nateglinide ester (10 grams, 0.032 moles) at room temperature. 2.5N NaOH solution (15 ml) was added drop wise to reaction mass within 30.0 min. The temperature of the reaction mass was maintained at 25 to 30° C. and stirred for 12 hours. The reaction mass was distilled under reduced pressure and the obtained residue was acidified to pH 2-3 to obtain the precipitate of nateglinide. The reaction mass was further stirred for 1 hour. The solid was isolated by filtration, washed with DI water till neutral pH, suck dried and dried at 80° C.

Yield=9.0 grams
Efficiency=93.75%
L-isomer=1.56%

Example 9

Preparation of Nateglinide in Methanol-Water

To a solution of Methanol (400.0 ml) and water (400.0 ml) was added Nateglinide ester (10 grams, 0.032 moles) at room temperature. 2.5N NaOH solution (30 ml) was added drop wise to reaction mass within 30.0 min. at 10° C. The temperature of the reaction mass was raised to 25-30° C. and stirred for 10 hours. The reaction mass was filtered to remove the undissolved particles. The filtrate was cooled to 10° C. and acidified to pH 2-3 to obtain the precipitate of nateglinide. The reaction mass was further stirred for 1 hour. The solid was isolated by filtration, washed with water till neutral pH, suck dried and dried at 80° C.

Yield=6.5 grams
Efficiency=67.7%
L-isomer=0.37%

Similar experiments were carried out using varied volumes of methanol: water at varied reaction conditions. The results are summarized in following Table 1.

TABLE 1

Temperature- and reaction time-related data

| Methanol Volume | Water Volume | NaOH Equivalent | Temperature | Reaction Hours | L-isomer (area %) | Efficiency |
|---|---|---|---|---|---|---|
| 40 | 40 | 2.5 | 20-25° C. | 12 | 0.4 | 68.0% |
| 10 | 20 | 2.5 | 20-25° C. | 24 | — | 50-60% unreacted ester |
| 10 | 20 | 4 | 20-25° C. | 24 | — | 50-60% unreacted ester |
| 5 | 20 | 2.5 | 20-25° C. | 24 | — | 50-60% unreacted ester |
| 5 | 20 | 4 | 20-25° C. | 24 | — | 50-60% unreacted ester |

Example 10

Preparation of Nateglinide in Water

To a solution of water (200.0 ml) and Nateglinide ester (10.0 grams, 0.03 moles) at room temperature cooled to 10° C., 2.5N NaOH solution (30 ml) was added drop wise to reaction mass within 30.0 min. The temperature of the reaction mass was raised to 45° C. and further stirred for 5-6 hours. The reaction mass was filtered through hyflo, washed hyflo bed with water (50.0 ml). The clear filtrate was further washed with (2×100.0 ml) dichloromethane and cooled to 10° C. followed by acidification to pH 2-3 with 2N HCl solution. The reaction mass was further stirred at 10° C. for 1 hours. The solid was isolated by filtration, washed with DI water till neutral pH, suck dried and dried at 80° C.

Yield=8.9 grams
Efficiency=92.7%
L-isomer=0.28%

Example 11

Preparation of Nateglinide in Acetone

To a solution of Acetone (200.0 ml) and Nateglinide ester (5.0 grams, 0.0151 moles) at room temperature, 2.5N NaOH solution (18 ml) was added drop wise to reaction mass within 30.0 min. at 10° C. The temperature of the reaction mass was raised to 25-30° C. and further stirred for 2-3 hours. The reaction mass was filtered through hyflo, washed hyflo bed with water (50.0 ml). The clear filtrate diluted with 400.0 ml water and cooled to 10° C. followed by acidification to pH 2-3 with 2N HCl solution. The reaction mass was further stirred at 10° C. for 1 hours. The solid was isolated by filtration, washed with DI water till neutral pH, suck dried and dried at 80° C.

Yield=4.5 grams
Efficiency=93.75%
L-isomer=0.44%

Similar experiments were carried out using varied conditions of temperature and reaction time. The results are summarized in following Table 2.

TABLE 2

| Temperature | Reaction Hours | L-isomer (area %) | Efficiency |
|---|---|---|---|
| 20-25° C. | 2 | 0.44 | 94.0% |
| 10-15° C. | 6 | 0.44 | 88.0% |

Example 12

Preparation of Nateglinide Form B in Acetone-Water

To a solution of Acetone (3.0 lit) and DI water (3.0 lit) was added Nateglinide methyl ester (152 grams, 0.46 moles) at room temperature. The reaction mass was cooled to 10° C. 1N NaOH solution (548 ml) was added drop wise to the reaction mass within 30 min. The reaction mass was further stirred at 10-15° C. for 15-16 hours. The reaction mass was filtered through hyflo, washed with DI water (3.0 lit). The clear filtrate was cooled to 10° C., acidified to pH 2-3 with 2N HCL solution (600 ml) and further stirred at 10° C. for 1 hours. The solid was isolated by filtration, washed with DI water till neutral pH and dried at 80° C. to yield nateglinide Form B.

Yield=136.0 grams
Efficiency=93.2%
L-isomer=0.07%
Chiral purity=99.93%

Figure 1:
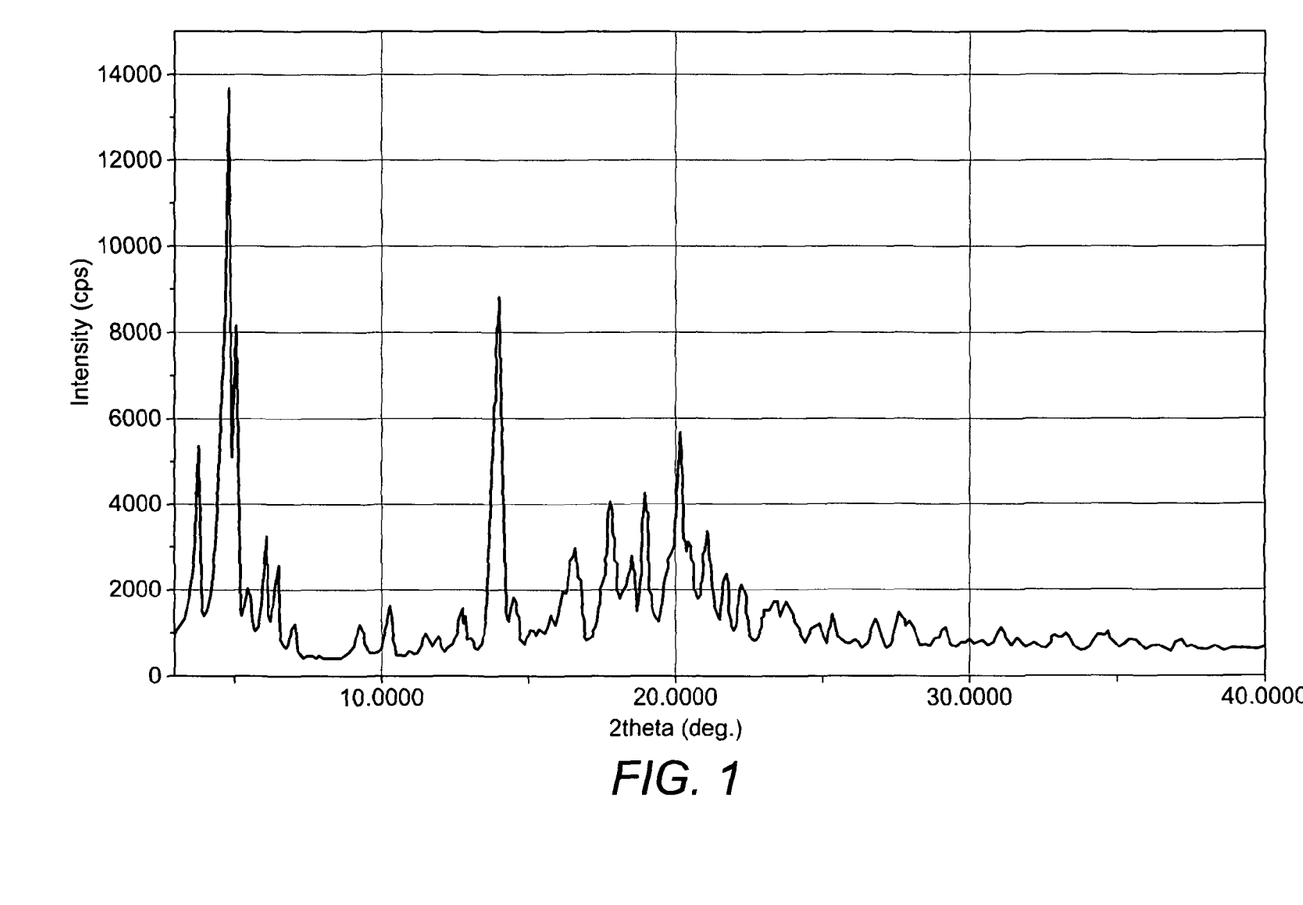
FIG. 1 shows a characteristic X-ray powder diffraction of nateglinide Form B obtained by an embodiment of the process of the present invention.

The XRPD pattern of the Form B is shown in FIG. 1. The parameters of the XRPD characterization are as follows.

The XRPD characterization was carried out on an Ultima IV model XRPD machine.

1. Source: Cu Kα
2. Scan axis: theta/2 theta
3. Voltage: 40 KV
4. Current: 30 mA
5. Measurement method: Continuous
6. Counting unit: CPS
7. Divergence slit: ⅔°
8. Receiving slit: 0.3 mm
9. Detector: Scintillation Counter
10. Wavelength: 1.5405 A°
11. Goniometer speed: 2°2θ/min.
12. Scanning range: 3° to 40° 2θ
13. Sampling width: 0.02° 2θ

It will be understood that the peak positions may vary by ±0.2° 2θ.

Figure 2:
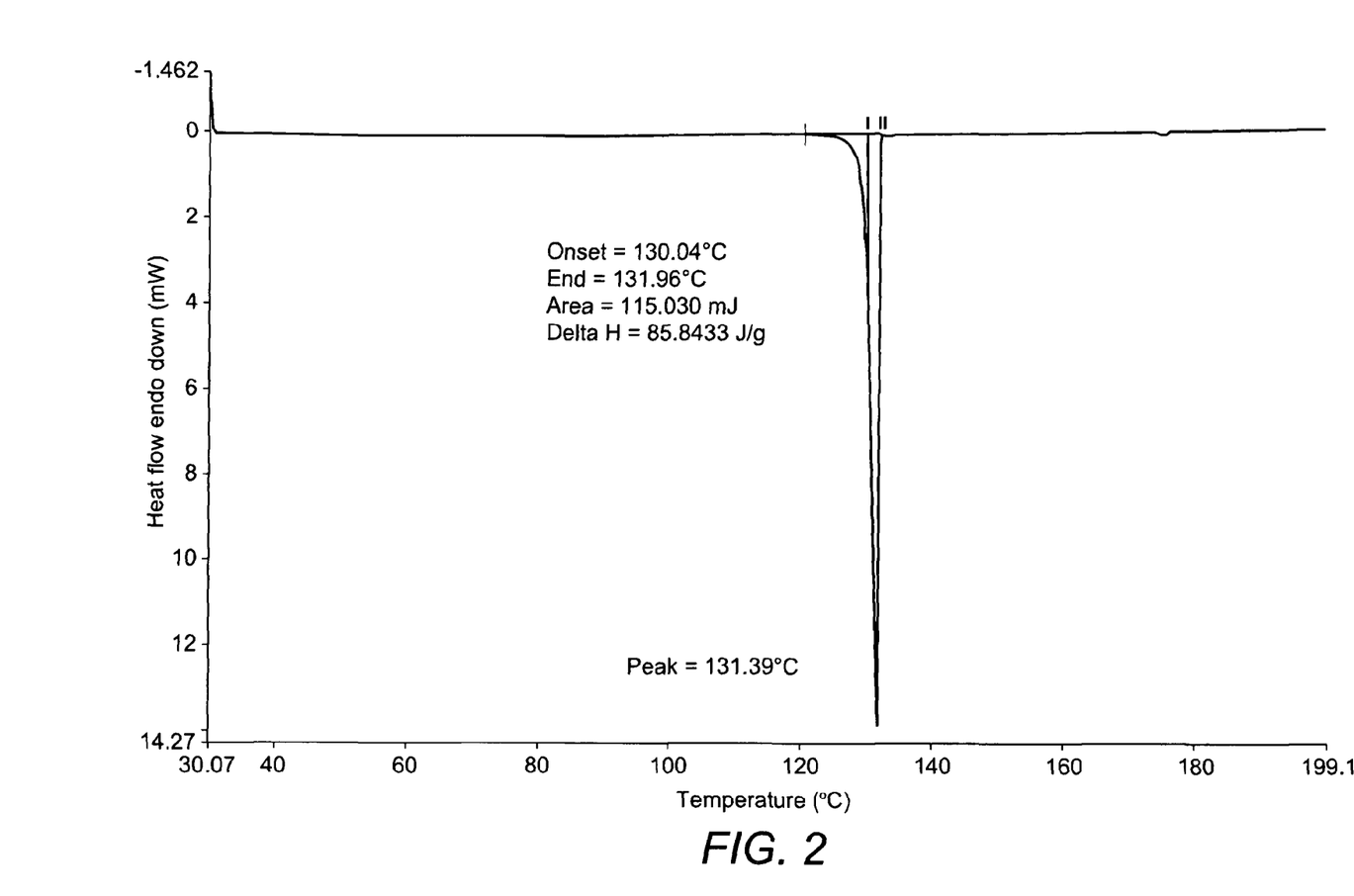
FIG. 2 shows a characteristic differential scanning calorimetric thermogram of nateglinide Form B obtained by an embodiment of the process of the present invention.

The DSC thermogram of the Form B is shown in FIG. 2. The parameters of the DSC characterization are as follows.

Start temperature: −50.00° C.
Stop temperature: 300° C.
Rate of Heating: −20° C./min Similar experiments were carried out using varied conditions of temperature and reaction time. The results are summarized in following Table 3.

TABLE 3

| Acetone Volume | Water Volume | Temperature | Reaction Hours | L-isomer | Efficiency |
|---|---|---|---|---|---|
| 20 | 20 | 10-15° C. | 16 | 0.08% | 93% |
| 20 | 20 | 15-20° C. | 6 | 0.09% | 92.7% |
| 20 | 20 | 20-25° C. | 4 | 0.13% | 92.8% |
| 20 | 20 | 25-30° C. | 4 | 0.18% | 93.0% |
| 20 | 20 | 30-35° C. | 4 | 0.23% | 92.1% |

Reference Example 13

Preparation of Nateglinide in IPA

To a solution of isopropyl alcohol (100.0 ml) and nateglinide methyl ester (10.0 grams, 0.0302 moles) at room temperature, 1N NaOH solution (50 ml) was added drop wise to the reaction mass and stirred for 6.0 hours. Completion of the reaction was monitored by TLC. The reaction mass was filtered and then diluted with 10.0 ml water and cooled to 10° C. and acidified to pH 2-3 with 2N HCl solution. The reaction mass was further stirred at 10° C. for 1 hours. The solid was isolated by filtration, washed with DI water till neutral pH, suck dried and dried at 80° C.
Yield=8.3 grams.
Efficiency=86.45%
L-isomer=0.22%

Reference Example 14

Preparation of Nateglinide in IPA

Nateglinide methyl ester (10.0 grams, 0.0302 moles) was stirred in 1N NaOH solution (50 ml) for 15-20 minutes at room temperature. Added isopropyl alcohol (100.0 ml) and the reaction mass was further stirred for 6.0 hours at ambient temperature. The reaction mass was diluted with water (100 ml) and acidified to pH 2 with HCl solution. The reaction mass was cooled to 10° C. The solid was isolated by filtration, and dried at 90° C. under vacuum.
Yield=8.2 grams
Efficiency=87%
L-isomer=0.24%

Example 15

Preparation of D-Phenyl Alanine Methyl Ester Hydrochloride Using Ethanolic HCl

To a 20% solution of ethanolic HCl (75 ml), was charged D-Phenyl alanine (15 grams, 0.090 moles). The reaction mass was further stirred for 48 to 50 hours at 25-30° C. (the reaction does not go to completion, shows 10-12% of unreacted D-Phenyl alanine) and concentrated at 50° C. under reduced pressure to form the residue. The residue was stirred in toluene (100 ml). The solid was isolated by filtration, washed with toluene (2×25 ml) and dried at 50-55° C. under vacuum to yield the desired product.
Yield=18 grams
Efficiency=86.28%

Example 16

Preparation of D-Phenyl Alanine Methyl Ester Hydrochloride Using Conc. Sulfuric Acid To a solution of methanol (150 ml), was charged D-Phenyl alanine (15 grams, 0.090 moles) and conc. Sulfuric acid (10 ml). The reaction mass was further stirred for 48 to 50 hours at 48-50° C. (the reaction does not go to completion, shows 10-12% of unreacted D-Phenyl alanine) and concentrated at 50° C. under reduced pressure to form the residue. The residue was stirred in toluene (100 ml). The solid was isolated by filtration, washed with toluene (2×25 ml) and dried at 50-55° C. under vacuum to yield the desired product.
Yield=20 grams
Efficiency=95.87%

It will be appreciated that the invention may be modified within the scope of the appended claims.

The invention claimed is:

1. A process for preparing nateglinide of formula (I) or a pharmaceutically-acceptable salt thereof, wherein the nateglinide is polymorphic Form B, which process comprises: preparing (−)-N-(trans-4-isopropylcyclohexyl-1-carbonyl)-D-phenylalanine alkyl ester of formula (II) by condensation of a D-phenylalanine alkyl ester of formula (IV) or an acid addition salt thereof with trans-4-isopropyl-cyclohexylcarboxylic acid of formula (III) in the presence of a condensation solvent, an alkali metal hydroxide and a condensing agent to form a (−)-N-(trans-4-isopropylcyclohexyl-1-carbonyl)-D-phenylalanine alkyl ester of formula (II) without intermediate conversion to an acid chloride or an N-hydroxysuccinmide ester, of formula (III)

wherein the Alk group is a $C_1$-$C_4$ alkyl group; and
hydrolysis of compound (II)

-continued (I)

in the presence of a hydrolysis solvent, wherein the hydrolysis solvent is a mixture of a ketone and water, and the ketone:water ratio varies from 5:1 to 1:1 v/v; and optionally conversion of the nateglinide (I) to a salt thereof.

2. The process according to claim 1, wherein Alk is methyl.

3. The process according to claim 1, wherein the hydrolysis is carried out at a temperature ranging from 0° C. to 30° C.

4. The process according to claim 1, wherein the hydrolysis solvent comprises acetone and water.

5. The process according to claim 1, wherein the hydrolysis solvent is a 1:1 v/v mixture of acetone and water, isolation of the nateglinide comprises drying under vacuum tray driers at a temperature ranging from 70° C. to 90° C.

6. The process according to claim 1, wherein the compound (IV) is in the form of an HCl addition salt.

7. The process according to claim 1, wherein the trans-4-isopropyl-cyclohexylcarboxylic acid of formula (III) is in molar excess relative to the compound (IV).

8. The process according to claim 1, wherein the condensing reagent is selected from the group consisting of phenylsilane, 1,1'-carbonyldiimidazole (CDI), benzotriazol-1-yloxytris (dimethylamino) phophonium hexafluorophosphate (BOP), 1-hydroxy benzotriazole hydrate (HOBt), PyBOP (Analog of the BOP), 1,3-dicyclohexylcarbodiimide (DCC), 1,3-diisopropylcarbodiimide (DIC), N,N-diisopropylethylamine (DIEA), 4-dimethylaminopyridine (DMAP), 1,4-dithio-L-threitol (DTT), N-ethyl-N'-(3-dimethylaminopropyl) carbodidimide hydrochloride (EDC HCl), 2-(7-aza-1H-benzotriazole-1-yl)-1,1,3,3-tetramethyluroniumhexafluorophosphate (HATU), 2-(1H-benzotriazole-1-yl)-1,1,3,3-tetramethyluronium hexafluorophosphate (HBTU), 2-(6-chloro-1H-benzotriazole-1-yl)-1,1,3,3-tetramethylaminiumhexafluorophosphate (HCTU), O-(benzotriazol-1-yl)-N,N,N',N'-tetra methyluronium tetrafluoroborate (TBTU), tetramethylfluoroformamidiniunhexafluorophosphate (TFFH) and mixtures thereof.

9. The process according to claim 8, wherein the condensing reagent is a mixture of DCC and HOBT.

10. The process according to claim 9, wherein 0.3 moles of HOBT per mole of compound (IV) are used in the condensation.

11. The process according to claim 1, wherein the condensation solvent is selected from the group consisting of chloroform, dichloromethane (MDC), dimethylformamide, dimethylacetamide, dimethyl sulfoxide, N-methyl pyrrolidone, sulfolane, diglyme, 1,4-dioxane, tetrahydrofuran, acetonitrile, acetone and mixtures thereof.

12. The process according to claim 11, wherein the condensation solvent is MDC.

13. The process according to claim 1, wherein the condensation step is carried out at a temperature ranging from −5 to 30° C.

14. The process according to claim 1, wherein the alkali metal hydroxide is selected from the group consisting of sodium hydroxide, potassium hydroxide, caecium hydroxide, magnesium hydroxide, lithium hydroxide, barium hydroxide and calcium hydroxide, preferably sodium hydroxide.

15. The process according to claim 1, wherein the reaction mass after hydrolysis is treated with HCl at 10° C. until the pH is adjusted to 2-3 to obtain nateglinide of formula (I).

16. The process according to claim 1, wherein the compound (II) is purified in C1-C4 alcohol prior to the hydrolysis step.

17. The process according to claim 1, wherein the compound (IV) or salt thereof is prepared by esterification of D-phenyl alanine of compound of formula (V)

(V)

with thionyl chloride in methanol to obtain the compound (IV) or salt thereof.

18. The process according to claim 17, wherein esterification is carried out at a temperature ranging from 0° to 30° C.

19. The process according to claim 17, wherein the compound (IV) is converted to the compound of formula (II) either by isolating the compound (IV) as an acid addition salt of formula (IVa) and using compound (IVa) in the condensation to form compound (II) or by preparing the compound (IV) as an acid addition salt of formula (IVa), converting compound (IVa) to the free base of formula (IVb) and using compound (IVb) in the condensation to form compound (II)

(IVa)

(IVb)

wherein X in compound (IVa) is an acid and Alk has the same meaning as defined in claim 1.

* * * * *

UNITED STATES PATENT AND TRADEMARK OFFICE
CERTIFICATE OF CORRECTION

| | |
|---|---|
| PATENT NO. | : 9,150,499 B2 |
| APPLICATION NO. | : 13/703758 |
| DATED | : October 6, 2015 |
| INVENTOR(S) | : Kankan et al. |

Page 1 of 1

It is certified that error appears in the above-identified patent and that said Letters Patent is hereby corrected as shown below:

In the Specification

Col. 13, Line 7, replace "stifling" with --stirring--.

Col. 13, after Line 10, insert --Yield =175.0 grams-- and shift subsequent lines down.

Signed and Sealed this
Seventeenth Day of May, 2016

Michelle K. Lee
*Director of the United States Patent and Trademark Office*